United States Patent [19]

Tipton et al.

[11] Patent Number: 5,747,058
[45] Date of Patent: May 5, 1998

[54] HIGH VISCOSITY LIQUID CONTROLLED DELIVERY SYSTEM

[75] Inventors: Arthur J. Tipton; Richard J. Holl, both of Birmingham, Ala.

[73] Assignee: Southern Biosystems, Inc., Birmingham, Ala.

[21] Appl. No.: 474,337

[22] Filed: Jun. 7, 1995

[51] Int. Cl.$^6$ .............................. A61F 2/02; A61F 6/06; A61F 9/02; A61L 9/04

[52] U.S. Cl. .............................. 424/423; 424/45; 424/430; 424/435; 424/436; 424/443; 424/451; 424/464

[58] Field of Search ............................. 424/45, 423, 430, 424/435, 436, 443, 451, 464

[56] References Cited

U.S. PATENT DOCUMENTS

| | | |
|---|---|---|
| 4,530,840 | 7/1985 | Tice et al. |
| 4,622,219 | 11/1986 | Haynes . |
| 4,725,442 | 2/1988 | Haynes . |
| 4,767,628 | 8/1988 | Hutchinson . |
| 4,891,225 | 1/1990 | Langer . |
| 4,906,474 | 3/1990 | Langer . |
| 4,938,763 | 7/1990 | Dunn et al. |
| 4,957,744 | 9/1990 | Della Valle et al. |
| 5,149,543 | 9/1992 | Cohen . |
| 5,324,520 | 6/1994 | Dunn et al. |
| 5,330,835 | 7/1994 | Kikuchi et al. |
| 5,340,572 | 8/1994 | Patel et al. ............................ 424/78.04 |

FOREIGN PATENT DOCUMENTS

| | | |
|---|---|---|
| 2096516 | 9/1988 | Japan . |
| 7115901 | 10/1993 | Japan . |

OTHER PUBLICATIONS

Desai, Neil P., et al., "Surface Modification of Polymeric Biomaterials for Reduced Thrombogenicity," *Polym. Mater. Sci. Eng.*, 62:731–735.

Kulkarni et al., "Polylactic Acid for Surgical Implants," *Arch. Surg.*,, 93:389 (1966).

Henry, Chuck, "Sucrose Acetate Isobutyrate Special Grade for Beverage Applications,".

Material Safety Data Sheet of Eastman Fine Chemical Pharmaceutical Ingredients, "Sucrose Acetate Isobutyrate, Special Grade (SAIB–SG)," Publication No. EFC–211, (May 1991).

Material Safety Data Sheet of Eastman Products for the Food Industry, "Sucrose Acetate Isobutyrate (SAIB–SG) for Use in Fruit–Flavored Beverages," Publication No. ZM–90, pp. 2–7 (Sep. 1989).

Material Safety Data Sheet of Eastman Chemical Products, "SAIB Sucrose Acetate Isobutyrate," pp. 2–118.

*Primary Examiner*—Carlos A. Azpuru
*Attorney, Agent, or Firm*—Kilpatrick Stockton LLP; Roy D. Meredith, Esq.

[57] ABSTRACT

A composition for the controlled release of substances is provided that includes: (i) a non-polymeric, non-water soluble liquid carrier material (HVLCM) of viscosity of at least 5,000 cP at 37° C. that does not crystallize neat under ambient or physiological conditions; and (ii) a substance to be delivered.

95 Claims, 9 Drawing Sheets

HIGH VISCOSITY LIQUID CONTROLLED DELIVERY SYSTEM

This invention is a high viscosity liquid composition useful for the delivery of substances and for other applications, including the coating of tissue and the prevention of adhesions.

BACKGROUND OF THE INVENTION

There has been extensive research in the area of biodegradable controlled release systems for bioactive compounds. Biodegradable matrices for drug delivery are useful because they obviate the need to remove the drug-depleted device.

The most common matrix materials for drug delivery are polymers. The field of biodegradable polymers has developed rapidly since the synthesis and biodegradability of polylactic acid was reported by Kulkarni et al., in 1966 ("Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers).

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et al.; (1991) "Surface modification of polymeric biomaterials for reduced thrombogenicity," Polym. Mater. Sci. Eng., 62:731–735]).

Biodegradable hydrogels have also been developed for use in controlled drug delivery as carriers of biologically active materials such as hormones, enzymes, antibiotics, antineoplastic agents, and cell suspensions. Temporary preservation of functional properties of a carried species, as well as the controlled release of the species into local tissues or systemic circulation, have been achieved. See for example, U.S. Pat. No. 5,149,543 to Cohen. Proper choice of hydrogel macromers can produce membranes with a range of permeability, pore sizes and degradation rates suitable for a variety of applications in surgery, medical diagnosis and treatment.

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few nanometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a non-reactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

While a number of materials have been evaluated for use in the controlled delivery of substances, there remains a need to provide more simple systems with low toxicity for the controlled delivery of substances. The delivery systems described above, for example, require the preparation of polymers and loaded polymeric matrices, or hydrogels, or other complex or fragile compositions. In particular, there is a need to provide a liquid-based delivery system that is easily formulated with a substance to be delivered and easily administered.

Therefore, it is an object of the invention to provide a simple system for the delivery of substances.

It is another object of the invention to provide a liquid-based delivery system that is easily formulated with a substance to be delivered and easily administered.

It is another object of the present invention to provide a method for the controlled delivery of substances in a simple liquid-based system.

SUMMARY OF THE INVENTION

A composition for the controlled release of substances is provided that includes: (i) a non-polymeric, non-water soluble high-viscosity liquid carrier material (HVLCM) of viscosity of at least 5,000 cP at 37° C. that does not crystallize neat under ambient or physiological conditions; and (ii) a substance to be delivered.

In one embodiment, the HVLCM is mixed with a viscosity lowering water soluble or miscible solvent such as ethanol, dimethylsulfoxide, ethyl lactate, ethyl acetate, benzyl alcohol, triacetin, N-methylpyrrolidone, propylene carbonate, glycofurol, freons such as trichlorofluoromethane and dichlorofluoromethane, dimethyl ether, propane, butane, dimethyl formamide, dimethyl acetamide, diethylene carbonate, butylene glycol, N-(beta-hydromethyl)lactamide, dioxolanes, and other amides, esters, ethers, alcohols, to form a lower viscosity liquid carrier material (LVLCM), which is mixed with the substance to be delivered, prior to administration. In a preferred embodiment, the LVLCM has a viscosity less than 1000 cP. On administration, the composition is placed into the body or on a surface, and the solvent dissipates or diffuses away from the LVLCM, forming in-situ a highly viscous implant or composition that releases the substance over time. By appropriate selection of the solvent and the HVLCM, a wide variety of pre- and post-administration composition viscosities can be achieved. In a preferred embodiment, the HVLCM is biodegradable.

In one embodiment, the substance which is mixed with the HVLCM is a biologically active substance useful for human therapy, veterinary therapy, or for agricultural purposes. In the agricultural area, for example, the composition with appropriate active agents can be applied onto areas for the control of weeds (diquat, for example), insects (e.g., methylparathion), or pests. In the veterinary area, the composition can be used, for example, to deliver mixed steroids as growth promotants for cattle, or for the delivery of vaccines (such as parvovirus vaccine for the post-maternal protection of swine). In humans the composition can be used for the delivery of a wide range of biologically active substances, described in more detail below, or alternatively, can be used with or without active agents to block surgical adhesions or for scaffolding for void filling, or for guided tissue regeneration products, such as a periodontal membrane. In another example, the compositions could be injected into the arterial supply of a tumor, where it would form a highly viscous implant that would block the blood supply of the tumor. In another example, the composition could be used as a tissue adhesive, with or without sutures. In another example, the composition could be used as a partially occlusive covering for wounds.

In vivo implants of the composition can be placed anywhere within the body, including soft tissue such as muscle or fat; hard tissue such as bone; a cavity, including but not limited to the periodontal, oral, vaginal, rectal, or nasal cavity; or a pocket such as the periodontal pocket or the cul-de-sac of the eye.

The composition optionally includes additives that modify the properties of the composition as desired. Non-limiting examples of suitable additives include biodegradable polymers, non-biodegradable polymers, natural or synthetic oils, carbohydrates or carbohydrate derivatives, inorganic salts, BSA (bovine serum albumin), surfactants, and organic compounds, such as sugars, and organic salts, such as sodium citrate. In general, the less water soluble, i.e., more lipophilic, the additive, the more it will decrease the rate of release of the substrate, compared to the same composition without the additive. In one embodiment, it is desirable to use additives that increase properties such as the strength or the porosity of the composition. In one embodiment, the HVLCM or LVLCM is used in combination with an additive and without a substrate to be delivered.

In an alternative embodiment, the HVCLM/substrate composition is included in a second carrier material, for ease of storage, handling, delivery, or to otherwise modify one or more of the properties of the composition. Nonlimiting examples of second carrier materials are liquids that the HVLCM is not soluble in (forming an emulsion), solids, gel formulations, and transdermal delivery systems. The substrate should have high solubility in the HVLCM and low solubility in the second carrier material.

For example, an emulsion of HVCLM/substrate in water can be provided. A useful emulsion falling within this invention is a mouthwash, in which the substrate is an active agent for the treatment of halitosis, oral infections, or other oral disorders.

In another embodiment, the HVLCM is used as a carrier for the topical administration of a substrate. For example, the HVLCM can aid solubility and dermal transport of biologically active agents. In another example, the HVLCM could be used as a carrier for an insect repellant containing DEET. In another embodiment, the HVLCM is used to deliver compounds to hair or the scalp, for example anti-lice or anti-dandruff compounds, or therapeutic compounds.

DETAILED DESCRIPTION OF THE INVENTION

Figure 1:
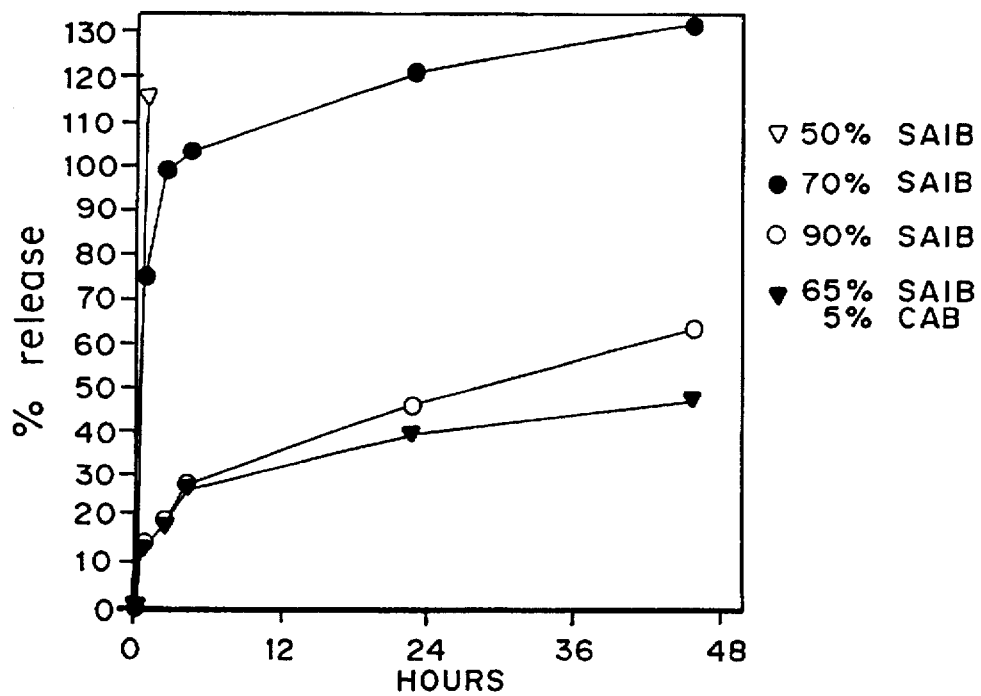
FIG. 1 is a graph of the release of methylene blue from SAIB (sucrose acetate isobutyrate) as measured in percent release over time (hours) (80% SAIB, closed circle; 85% SAIB, closed downward-pointing triangle; 90% SAIB, open square; 95% SAIB, upward-pointing triangle).
Figure 2:
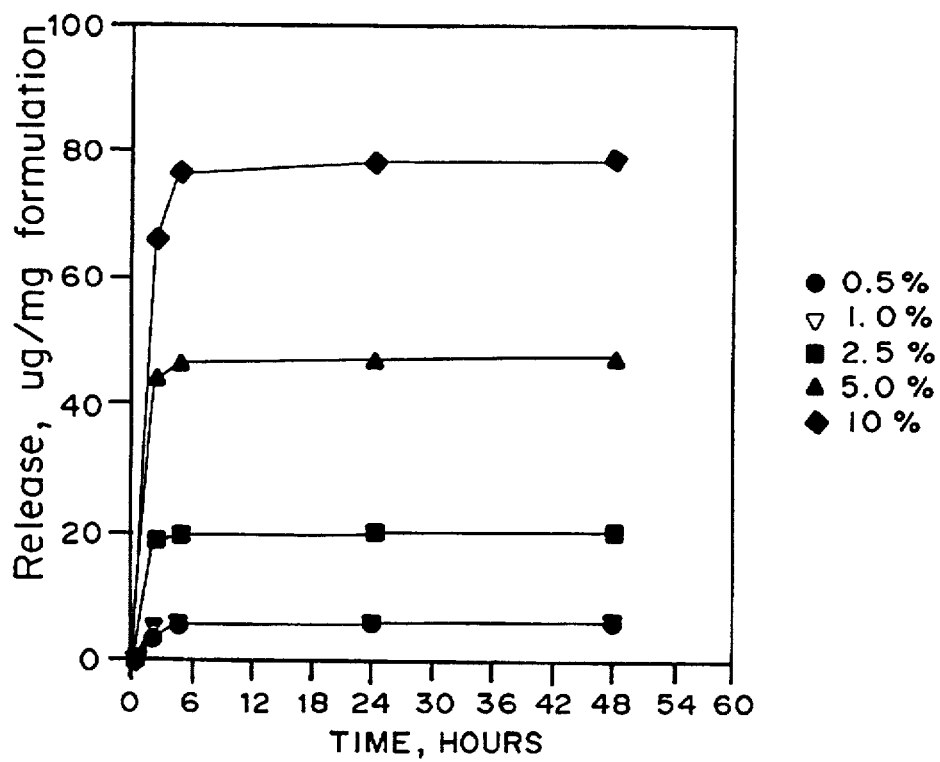
FIG. 2 is a graph of the release of theophylline from SAIB as measured in release (μg/mg) over time (hours) (0.5% theophylline, closed circle; 1.0% theophylline, downward-pointing triangle; 2.5% theophylline, closed square; 5.0% theophylline, upward-pointing triangle; 10% theophylline, closed diamond).
Figure 3:
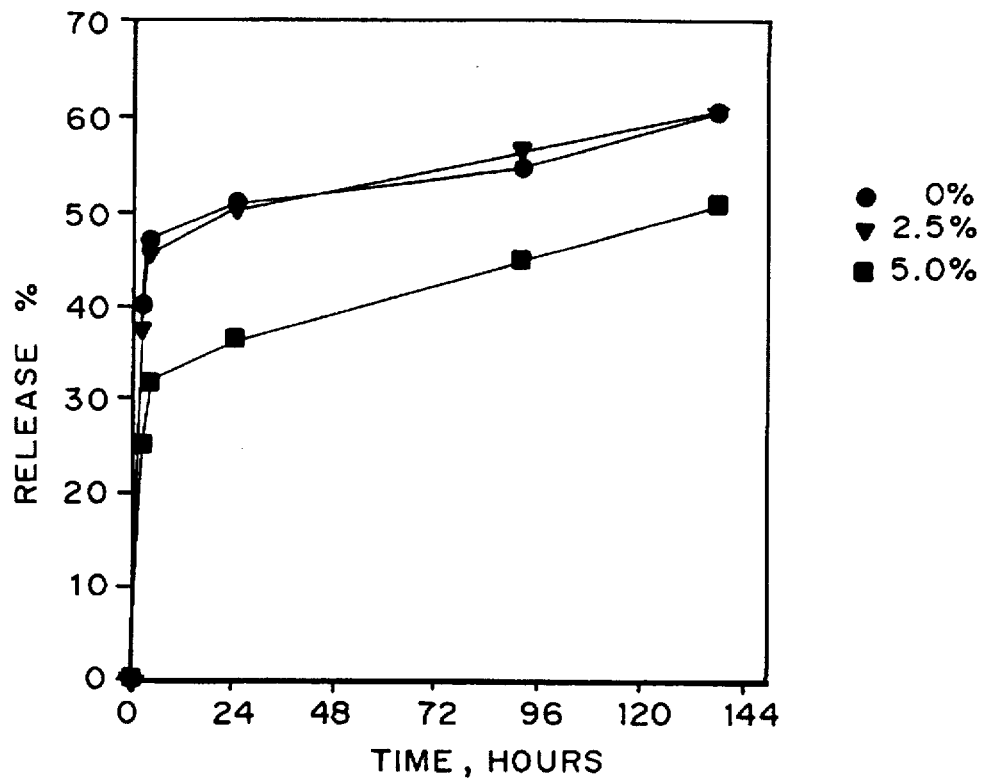
FIG. 3 illustrates the effect of sucrose on the release of methylene blue from 90% SAIB in percent release over time in hours (closed circle, 0% sucrose (90% SAIB, 10% EtOH); downward-pointing triangle, 2.5% sucrose (90% SAIB, 7.5% EtOH); closed square, 5.0% sucrose (90% SAIB, 5% EtOH)).
Figure 4:
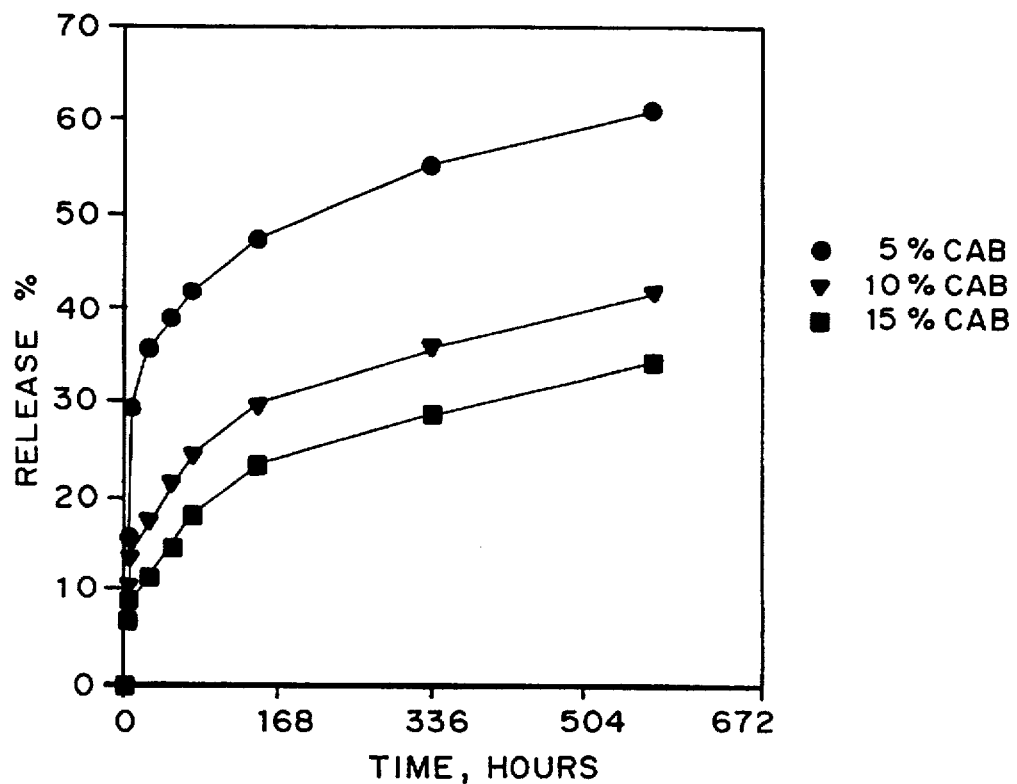
FIG. 4 illustrates the effect of CAB (cellulose acetate butyrate) on the release of methylene blue from SAIB, as measured in percent release over time (hours) (solid circle, 5% CAB (SAIB 40%, EtOH 55%); solid downward-pointing triangle, 10% CAB (SAIB 40%, EtOH 50%); and solid square, 15% CAB (SAIB 40%, EtOH 45%)).

I. Selection of High Viscosity Liquid Carrier Material

A high viscosity liquid carrier material should be selected that is non-polymeric, non-water soluble, and has a viscosity of at least 5,000 cP, (and optionally at least 10,000, 15,000; 20,000; 25,000 or even 50,000 cP) at 37° C. that does not crystallize neat under ambient or physiological conditions. The term non-water soluble refers to a material that is soluble in water to a degree of less than one percent by weight under ambient conditions.

In a preferred embodiment, the HVLCM significantly decreases in viscosity when mixed with a solvent to form a LVLCM that can be mixed with a substrate for controlled delivery. The LVLCM/substrate composition is typically easier to place in the body than a HVLCM/substrate composition, because it flows more easily into and out of syringes or other implantation means, and can easily be formulated as an emulsion. The LVLCM can have any desired viscosity. It has been found that a viscosity range for the LVLCM of less than approximately 1000 cP, and more particularly less than 200 cP, is typically useful for in vivo applications.

In a preferred embodiment, sucrose acetate isobutyrate ("SAIB"), a sucrose molecule esterified with two acetic acid and six isobutyric acid moieties, is used as the HVLCM. The structure of SAIB is set forth below.

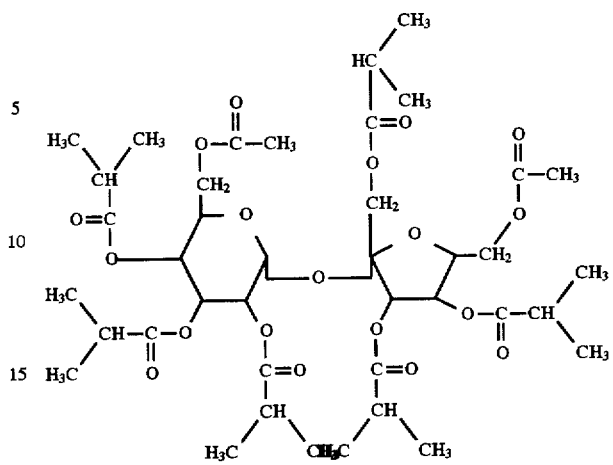

SAIB is orally non-toxic and is currently used as to stabilize emulsions in the food industry. It is a very viscous liquid and has an unusual property that there is a dramatic change in viscosity with small additions of heat or with the addition of solvents. It is soluble in a large number of biocompatible solvents. When in solution or in an emulsion, SAIB can be applied via injection or an aerosol spray. SAIB is compatible with cellulose esters and other polymers that can affect the rate of delivery of the substance.

In other embodiments, the HVLCM can be stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, beheny erucate, and glyceryl phosphates. In a particular embodiment, the HVLCM is acetylated sucrose distearate (Crodesta A-10).

The HVLCM is present in the composition in any amount that achieves the desired affect. For example, as a tissue coating or for the prevention of adhesions, the HVLCM can be used alone as a protective film or bolus, or with a substrate that enhances the properties or effect of the material. The HVLCM is typically present in controlled delivery compositions in an amount in the range from about 99.5 percent to about 10 percent by weight, more typically, between 95 and 25 percent, and most typically, between 85 and 45, relative to the total weight of the composition.

II. Substance to be Delivered

Any substance that exhibits a desired property can be delivered using this process. Preferably, the substance is a biologically active substance.

The term biologically active substance as used herein refers to an organic molecule including a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or combination thereof, that causes a biological effect when administered in vivo to an animal, including but not limited to birds and mammals, including humans.

The term drug, as used herein, refers to any substance used internally or externally as a medicine for the treatment, cure, or prevention of a disease or disorder, and includes but is not limited to immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers.

The term biologically active substance also includes agents such as insecticides, pesticides, fungicides, rodenticides, and plant nutrients and growth promoters.

In one embodiment, the composition is a vaccine and the substance to be delivered is an antigen. The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell-mediated. In the event the material to which the immunogenic response is to be directed is poorly antigenic, it may be conjugated to a carrier such as albumin or to a hapten, using standard covalent binding techniques, for example, with one of the several commercially available reagent kits.

Examples of preferred antigens include viral proteins such as influenza proteins, human immunodeficiency virus (HIV) proteins, and hepatitis A, B, or C proteins, and bacterial proteins, lipopolysaccharides such as gram negative bacterial cell walls and Neisseria gonorrhea proteins, and parvovirus.

Non-limiting examples of pharmacological materials include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, dyptheria toxoid, tetanus toxoid, pigeon pox, whooping cough, influenzae rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyl-testosterone and fluorymesterone; estrogens such as estrone, 17-β-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-β-hydroxyprogesterone; humoral agents such as the prostaglandins, for example $PGE_1$, $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers.

The active compound is included in the composition in an amount sufficient to deliver to the host animal or plant an effective amount to achieve a desired effect. The amount of drug or biologically active agent incorporated into the composition depends upon the desired release profile, the concentration of drug required for a biological effect, and the desired period of release of the drug.

The concentration of active compound in the composition will also depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The composition may be administered in one dosage, or may be divided into a number of smaller doses to be administered at varying intervals of time.

The biologically active substance is typically present in the composition in the range from about 0.5 percent to about 20 percent by weight relative to the total weight of the composition, and more typically, between approximately 1 percent to about 15 percent by weight, and more. Another preferred range is from about 2 percent to about 10 percent by weight. For very active agents, such as growth factors, preferred ranges are less than 1% by weight, and less than 0.0001%.

Both soluble and insoluble substances can be distributed in the HVLCM or LVLCM for controlled delivery.

III. Additives

A variety of additives can optionally be added to the HVLCM or LVLCM to modify the properties of the material as desired. The additives can be present in any amount which is sufficient to impart the desired properties to the composition. The amount of additive used will in general be a function of the nature of the additive and the effect to be achieved, and can be easily determined by the routineer.

When present, the additive is typically present in the compositions in an amount in the range from about 0.1 percent to about 20 percent by weight, relative to the total weight of the composition, and more typically, is present in the composition in an amount in the range from about 1, 2, or 5 percent to about 10 percent by weight. Certain additives, such as buffers, are only present in small amounts in the composition.

The following categories are nonlimiting examples of classes of additives that can be employed in the composition. Given the disclosure herein and the objects to be achieved, one of skill in the art will easily know how to select other additives to achieve a desired purpose. All of these embodiments are considered to fall within the disclosed invention.

A. Biodegradable Polymers

One category of additives are biodegradable polymers and oligomers. The polymers can be used to alter the release profile of the substance to be delivered, to add integrity to the composition, or to otherwise modify the properties of the composition. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybuty-ates, polyhydroxyvalerates, polyalkylene oxalates, polyalkylene succinates, poly(malic acid), chitin, chitosan, and copolymers, terpolymers, oxidized cellulose, or combinations or mixtures of the above materials.

Examples of poly($\alpha$-hydroxy acid)s include poly(glycolic acid), poly(DL-lactic acid) and poly(L-lactic acid), and their copolymers. Examples of polylactones include poly($\epsilon$-caprolactone), poly($\delta$-valerolactone) and poly(gamma-butyrolactone).

B. Non-biodegradable Polymers

Another additive for use with the present compositions are non-biodegradable polymers. Non-limiting examples of non-erodible polymers which can be used as additives include: polyacrylates, ethylene-vinyl acetate polymers, cellulose and cellulose derivatives, acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide.

Preferred non-biodegradable polymers include polyethylene, polyvinyl pyrrolidone, ethylene vinylacetate, polyethylene glycol, cellulose acetate butyrate ("CAB") and cellulose acetate propionate ("CAP").

C. Oils and Fats

A further class of additives which can be used in the present compositions are natural and synthetic oils and fats. Oils derived from animals or from plant seeds of nuts typically include glycerides of the fatty acids, chiefly oleic, palmitic, stearic, and linolenic. As a rule the more hydrogen the molecule contains, the thicker the oil becomes.

Non-limiting examples of suitable natural and synthetic oils include vegetable oil, peanut oil, medium chain triglycerides, soybean oil, almond oil, olive oil, sesame oil, peanut oil, fennel oil, camellia oil, corn oil, castor oil, cotton seed oil, and soybean oil, either crude or refined, and medium chain fatty acid triglycerides.

Fats are typically glyceryl esters of higher fatty acids such as stearic and palmitic. Such esters and their mixtures are solids at room temperatures and exhibit crystalline structure. Lard and tallow are examples. In general oils and fats increase the hydrophobicity of the SAIB, slowing degradation and water uptake.

D. Carbohydrates and Carbohydrate Derivatives

Another class of additives which can be used in the present compositions are carbohydrates and carbohydrate derivatives. Non-limiting examples of these compounds include monosaccarides (simple sugars such as fructose and its isomer glucose (dextrose); disaccharides such as sucrose, maltose, cellobiose, and lactose; and polysaccarides.

IV. Solvent

When the composition is used as a LVLCM, it should contain a solvent that the HVLCM is soluble in. Preferably, the substance to be delivered is also soluble in the solvent. The solvent should be non-toxic, water soluble or water miscible, and otherwise biocompatible. Solvents that are toxic should not be used for pharmaceutical or agricultural purposes. The solvents used to inject the composition into animals should not cause significant tissue irritation or necrosis at the site of implantation, unless irritation or necrosis is the desired effect.

The solvent should be at least water soluble, so that it will diffuse quickly into bodily fluids or other aqueous environment, causing the composition to coagulate or solidify. Examples of suitable solvents include ethanol, ethyl lactate, propylene carbonate, glycofurol, N-methylpyrrolidone, 2-pyrrolidone, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, and 1-dodecylazacycloheptan-2-one.

When SAIB is used as the HVLCM, the preferred solvents are ethanol, dimethylsulfoxide, ethyl lactate, ethyl acetate, benzyl alcohol, triacetin, N-methylpyrrolidone, propylene carbonate, and glycofurol. SAIB is not miscible with glycerol, corn oil, peanut oil, 1,2-propanediol, polyethylene glycol (PEG200), super refined sesame oil, and super refined peanut oil. Accordingly, the latter group of solvents are not preferred for use with SAIB.

The solvent is typically added to the compositions in an amount in the range from about 5 percent to about 55 percent by weight, relative to the total weight of the composition. Preferably, the solvent is present in the composition in an amount in the range from about 10 percent to about 50 percent by weight. Another preferred range is from about 10 percent to 30 percent by weight.

V. Uses of the LVLCM and HVLCM Compositions

The composition described herein can be administered to the host through a variety of methods which can vary depending on the result to be achieved. When the host is an animal, such as a human, the composition can be administered, for example, topically, systemically (for example, mucosally (orally, rectally, vaginally, or nasally), or parenterally (intravenously, subcutaneously, intra muscularly, or intraperitoneally) in an appropriate carrier, if desired. When the composition is used for agricultural purposes, it can be applied via pouring, spray, dip, aerosol, or coating applicator.

Preferably, for pharmaceutical or veterinary purposes, the present compositions are administered as solutions via injection, or in an aerosol, paste or emulsion. When administered via injection as a LVLCM, the small amount of solvent used in the composition leaches into the aqueous fluid of the host, forming a highly viscous depot for the controlled delivery of substances or a coating for tissue that can prevent or minimize adhesions. When used in an aerosol or in an emulsion, the small amount of solvent in the solution evaporates upon application allowing the LVLCM to set-up as an HVLCM. Formation of aerosols and emulsions can be accomplished using techniques known to those skilled in the art. See, for example, Ansel, H. C. et al., *Pharmaceutical Dosage Forms and Drug Delivery Systems*, sixth ed., 1995.

The compositions can be used to form protective tissue coatings, and in particular, can be used to prevent the formation of surgical adhesions. The HVLCM can adhere to the surrounding tissue or bone, and can thus be injected subdermally like collagen to build up tissue or to fill in defects. It can also be injected into wounds including burn wounds to prevent the formation of deep scars. The degradation time of the HVLCM can be modulated, for example, by using a polymer as an additive to the HVLCM. Then the implant formed by the HVLCM will slowly biodegrade within the body and allow natural tissue to grow and replace the impact as it disappears.

Topical Oral Delivery composition

A topical oral delivery system can be prepared according to this invention that comprises a surfactant, a cosurfactant, an oily component, an HVLCM, for example, sucrose acetate isobutyrate, and water capable of sustaining the delivery of the active agent to the oral cavity.

This invention can be used, for example, to formulate a long-acting mouthwash containing SAIB and an active agent in a water based second carrier material in emulsion form. If the mouthwash is used in the conventional manner before going to bed, for example, there is a reduction in halitosis the following morning.

The components in the formulation of the mouthwash can be categorized into six groups: antimicrobial actives; surfactants; cosurfactants; oily components; sucrose acetate isobutyrate; water; and additives. Each of these groups are addressed in detail below. Given this disclosure one of ordinary skill can prepare other topical oral delivery systems for a wide range of applications, including for the treatment of oral infections and other oral disorders, by selection of the appropriate active agent.

Antimicrobial Actives

Antimicrobial active agents that are currently used in mouthwash formulations can include, but not limited to, domiphen bromide, triclosan, chlorhexidine, essential oils, cetyl pyridinium chloride, fluorides, alexidine, salicylanilides, zinc compounds, and antibiotics. They can be used either singly or in combination. Cetyl pyridinium chloride and zinc compounds particularly zinc gluconate are preferred.

Surfactant

In general, the surfactant selected for use in the formulations of the present invention are water-soluble and nonionic including but not limited to polyoxyethylene castor oil, polyoxyethylene hydrogenated castor oil, polyoxyethylene sorbitan fatty acid esters, polyoxyethylene alkyl esters, polyoxyethylene alkyl ethers, polyoxyethylene glycerol esters, and sorbitan fatty acid esters, used separately or in combination. Preferred nonionic surfactant are polyoxyethylene sorbitan fatty acid esters with 5–40 moles of ethylene oxide and polyoxyethylene glyceryl esters with 5–20 moles of ethylene oxide. Particularly preferred are polyoxyethylene (20 E.O.) sorbitan monooleate, polyoxyethylene (20 E.O.) almond oil, polyoxyethylene (20 E.O.) hydrogenated castor oil, and the like.

The amount of the surfactant to be incorporated in the formulations of the present invention varies depending on the type of surfactant used. In generally, a preferable range is 1–60 wt percent, with particularly preferable range being 2–10 wt percent.

Cosurfactant

In general, the cosurfactant used in the formulations of the present invention is designated as the alcohol or low hydrophilic/lipophilic balance (HLB) nonionic component of the surfactant/cosurfactant system. In the formulation of the present invention, cosurfactants having function as solubilizers or cosolvents, besides having function as surfactant, are preferred. Monohydric or polyhydric alcohols or low HLB nonionic surfactant may be used as such cosurfactant either singly or in combinations of two or more of them. Given as examples of monohydric alcohols are benzyl alcohol, ethyl alcohol, octyl alcohol, and the like; and as examples of polyhydric alcohols are propylene glycol, glycerine, 1,3-butylene glycol, and the like. Given as examples of low HLB nonionic surfactant are distilled monoglycerides, polyglycerol polyoleates, and polyethylene glycols with molecular weights between 300–4,000. Given as more preferable examples of cosurfactant are polyglycerol polyoleates. Included in particularly preferable cosurfactant are decaglyceryl tetraoleate.

The amount of these cosurfactant to be incorporated in the formulations of the present invention varies depending on the type of cosurfactant used. In general, a preferable range is 0.5–30 wt %, with particularly preferable range being 1–5 wt %.

Oily Components

One or more oily components typically selected from the group consisting of glycerine fatty acid esters, fatty acid esters, fatty alcohols and their derivatives, fatty alcohol benzoates, and Hydrocarbons can be used as the oily component in the formulations of the present invention. Acceptable mono-, di-, or triglycerides or their mixtures can be used as the glycerine fatty acid ester, irrespective of their sources or origins, whether they are naturally occurring or synthetic compounds, or semi-synthetic compounds. Preferred glycerine fatty acid esters are almond oil, olive oil, sesame oil, peanut oil, fennel oil, camellia oil, corn oil, castor oil, cotton seed oil, and soybean oil, either crude or refined, and medium chain fatty acid triglycerides, alone or in combination. Particularly preferred are medium chain fatty acid triglycerides.

Preferable fatty acid esters are isopropyl myristate, octyl palminate, ethyl oleate, and ethyl palmitate. Particularly preferred are isopropyl myristate and octyl palmitate. Particularly preferred fatty alcohol derivatives and fatty alcohol benzoates are 2-octyl dodecanol and $C_{12-15}$ alcohol benzoate. Light or heavy liquid paraffin oil are given as the preferred hydrocarbon.

The oily components can be used singly or in combinations with other oily components. These oily components may be incorporated in the formulations of the present invention in an amount of 0.5–50 wt %, and preferably 1–10 wt %.

Sucrose acetate isobutyrate

Sucrose acetate isobutyrate, described in detail above, is used as the HVLCM. SAIB is typically incorporated in the formulation in an amount of 0.01–10 wt %, and preferably 0.1–2 wt %.

Water

Another essential component of the formulations of the mouthwash is water. The formulations of the present invention has a pH of 3–10, preferably 5–9, and more preferably 6–8. Buffering agents can be used to maintain the pH in the above range. Acetic acid, citric acid, phosphoric acid, benzoic acid and/or their salts are given as examples of preferred buffering agents. The pH can be adjusted during manufacturing to the preferred range by the addition of suitable acid or base, preferably hydrochloric acid or sodium hydroxide, depending adjustment required. It is also preferred that the water used in the formulations of the present invention be deionized and filtered.

Additives

Other components, such as preservatives, stabilizers, antioxidants, coloring agents, isotonic agents, flavorings, humectants, sequesterants, vitamins and vitamin precursors, and the like, may be added as needed. As preferred examples of preservatives, paraben derivatives are given with methyl paraben and propyl paraben given as most preferred preservatives. As preferred examples of anti-oxidants, butyl hydroxyanisole, butyl hydroxytoluene, propyl gallate, vitamin E acetate, and purified hydroquinone are given with vitamin E acetate and butyl hydroxytoluene given as most preferred anti-oxidants. Given as preferred examples of humectant is sorbitol. Given as preferred examples of flavorings are peppermint oil, spearmint oil, wintergreen oil, menthol and saccharin. Given as preferred examples of sequesterant is citric acid.

The topical oral delivery systems can be prepared according to a conventional method, for example, by separately blending the oil phase and the water phase, and then combining the two phases at elevated temperature. The mixture of oil and water phases is then thoroughly mixed and cooled to room temperature before packaging.

VI. Examples

Given the disclosure herein, one of ordinary skill in the art will be able to prepare and use a wide variety of HVLCM compositions. It is intended that all of these various embodiments fall within the scope of this invention. The following examples, for ease of illustration, describe in detail the preparation and use of SAIB compositions. Other HVLCMs, additives, substrates and solvents can be used in like or similar manner.

The following general procedure was used to prepare the desired formulations in the Examples. Formulations were made in 20 mL scintillation vials and shaken, stirred, and/or heated to dissolve the biologically active substance in the SAIB/solvent system. In the Examples where the biologically active substance did not dissolve, the formulations were refrigerated and stirred to get the best distribution of biologically active substance in droplets.

The in vitro release of the biologically active compound was determined using the following general procedure. Phosphate-buffered saline ("PBS") (10 mL) of either pH 7.4 or pH 6.8 was added to a 16×25mm test tube. The pH of the PBS, 7.4 or 6.8, was selected based upon the application and solubility of the biologically active substance. The PBS included 0.2% sodium azide to prevent the growth of microorganisms. From 0.03 to 0.09 grams of the SAIB/Solvent/biologically active substance formulation was expelled from a disposable plastic pipette into the test tube, and the weight was recorded. The test tubes were capped and placed in a shaker bath set at 37° C. with constant shaking.

The test tubes were periodically removed from the shaker bath at various time points. At that time, the PBS was removed from the test tube containing the formulation and placed in a clean, dry test tube. These samples were UV analyzed to determine the amount of biologically active material in the PBS solution. Fresh PBS was placed in the test tube containing the formulation, which was then returned to shaker bath. This procedure was repeated at the various time points for which samples were obtained.

The concentration of the biologically active material in the release solutions was used to construct release profiles, based on the original amount of biologically active material in the formulation. This amount was determined using UV-visible spectrophotometry.

A variety of solvents were used in these examples, including: ethanol (EtOH), dimethylsulfoxide (DMSO), ethyl lactate (EtLac), ethyl acetate (EtOAc), benzyl alcohol ($\Phi CH_2OH$), triacetin, N-methylpyrrolidone (NMP), propylene carbonate (PC), and glycofurol (GF).

Larger percentages of solvent generally provided a greater concentration of biologically active substance in the formulation. The amount and type of the solvent are also directly related to viscosity of the solution. Table 1 sets out the effect of solvent and concentration on a SAIB/solvent mixture. The viscosity data was obtained using a Cannon-Fenske viscometer of size 200 at 30° C.

TABLE 1

| Material | Centipoise |
| --- | --- |
| rodiH$_2$O | 1.0 |
| EtOH | 1.3 |
| 60/40 SAIB/EtOH | 7.7 |
| 70/30 SAIB/EtOH | 17.0 |
| 55/40/5 SAIB/EtOH/CAB | 68.9 |
| 90/10 SAIB/EtOH | 494.8 |
| PC | 2.1 |
| 70/30 SAIB/PC | 138.7 |
| 70/30 SAIB/glycofurol | 228.4 |
| Peanut oil | 57.8 |

Effect of the Biologically Active Substance

Methylene blue and bovine serum albumin (BSA) were used to demonstrate drug release. Biologically active compounds released from the system included chlorhexidine, diclofenac, doxycycline, flurbiprofen, naproxen, and theophylline. Due to low water solubility of clotrimazole, release was not continued.

EXAMPLE 1

Ethanol (1 g.) was combined with sucrose acetate isobutyrate (SAIB) (9 g.). After gentle mixing, a clear, low-viscosity solution was obtained. A drop of this solution expelled from a glass pipet into water, formed a spherical matrix which held its shape for more than one week.

EXAMPLE 2

Ethanol (2 g.) were combined with SAIB (8 g.). The resulting solution, when mixed with water, formed a thin film. The film retained its shape longer than one week.

EXAMPLE 3

Solutions were prepared of varying amounts of ethanol and SAIB according to the process of Example 1. To this solution 0.07% methylene blue was added. Spherical drops were prepared, in phosphate buffered saline (PBS), as described in Example 1. The PBS samples were maintained at 37° C. At regular intervals the PBS was removed and analyzed for methylene blue content by ultraviolet-visible spectrophotometry. The results of the release of methylene blue are show in FIG. 1.

EXAMPLE 4

A series of formulations were prepared according to the process of Example 3, using bovine serum albumin (BSA) instead of methylene blue. Various percentages of BSA, solvents and SAIB were used in these formulations. The identity of the solvents and the ratios of BSA, solvent, SAIB and any additives, are set forth below in Tables 2 through 4. BSA release slowed with increasing ratios of CAP:SAIB.

BSA was not soluble in the system. Attempts were made with mixed solvents to solubilize it, but BSA was only soluble in glycerol and water which are not miscible with SAIB. All of the formulations containing BSA in the release profiles were non-homogeneous. Table 2 lists formulations containing BSA.

TABLE 2

| % BSA | % EtOH | % PVP | % 50/50 glycerol/DMSO |
|---|---|---|---|
| 27 | 37 | 0 | 4.4 |
| 4.6 | 36 | 0 | 5.6 |
| 5.5 | 36 | 0 | 5.8 |
| 5.0 | 33 | 5.9 | 6.9 |
| 5.5 | 31 | 8.2 | 8.3 |
| 4.9 | 27 | 18.8 | 9.8 |

TABLE 3

| % BSA | Solvent | % solv | additive | % add |
|---|---|---|---|---|
| 1.1 | PC | 31.3 | diH2O | 9.8 |
| 9.2 | no solvent was used (a paste of BSA/SAIB) | | | |
| 9.6 | glycerol | 9.2 | — | — |
| 1.9 | EtOH | 30 | — | — |
| 1.9 | EtOH | 20 | — | — |
| 1.9 | EtOH | 10 | — | — |
| 10 | EtOH | 10 | — | — |

Figure 5:
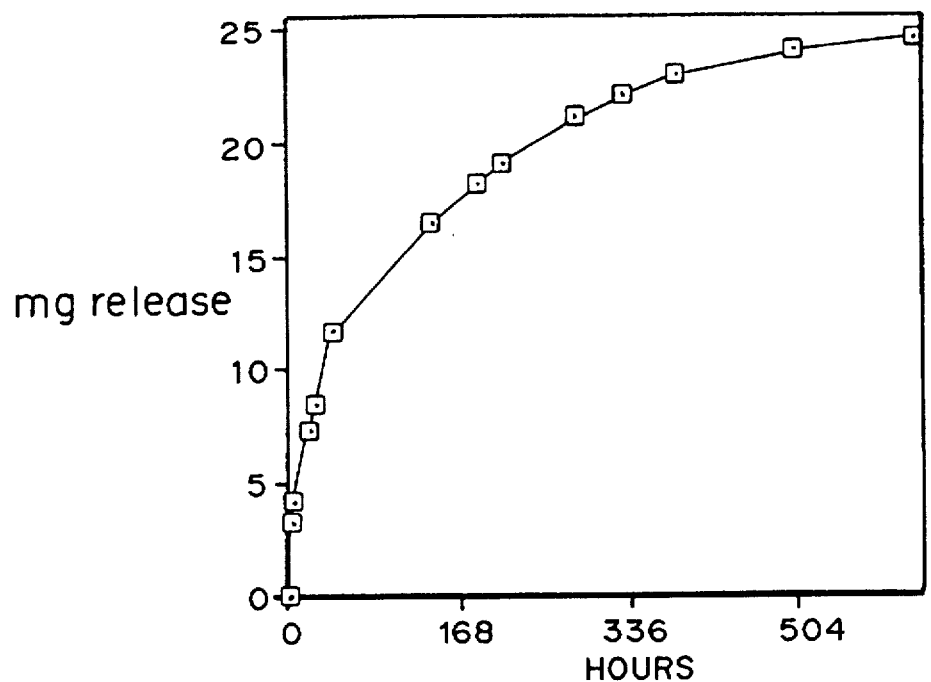
FIG. 5 is a graph of the release of BSA from a BSA(9%)/SAIB paste as measured in release (mg released) over time (hours).

FIG. 5 illustrates the release profile for the SAIB/BSA paste which was formed without the use of any additional solvent.

A release profile was attempted but not attained from the non-homogeneous formulations shown in Table 4.

TABLE 4

| % BSA | Solvent | % solv | additive | % add |
|---|---|---|---|---|
| 1 | EtOH | 9.6 | — | — |
| 1 | EtOH | 19 | — | — |
| 1 | EtOH | 29 | — | — |
| 1 | EtOH | 50 | — | — |
| 1 | EtOH | 89 | — | — |

EXAMPLE 5

The procedure of Example 3 was repeated using a series of formulations containing chlorhexidine as the biologically active agent. Formulations containing various amounts of solvent, SAIB and additives were prepared.

Formulations to which chlorhexidine was added as the biologically active substance are set forth below in Table 7.

TABLE 5

| % drug | Solvent | % solv | additive | % add | solubility |
|---|---|---|---|---|---|
| 5 | EtLac | 50 | — | — | insoluble |
| | | 30 | — | — | insoluble |
| | | 10 | — | — | insoluble |
| | NMP | 50 | — | — | soluble |
| | | 30 | — | — | insoluble |
| | | 10 | — | — | insoluble |
| | PC | 31 | — | — | insoluble |
| | | 20 | — | — | insoluble |
| | | 10 | — | — | insoluble |
| | EtOH | 50 | — | — | soluble |
| | | 30 | — | — | insoluble |
| | | 10 | — | — | insoluble |
| | | 45 | CAB | 5 | soluble |
| | | 40 | | | soluble |
| | | 35 | | | insoluble |
| 2.6 | | 23 | PVP | 5.1 | insoluble |
| 2.5 | | 23 | CAB | 5 | insoluble |

TABLE 5-continued

| % drug | Solvent | % solv | additive | % add | solubility |
|---|---|---|---|---|---|
| | | 23 | CAP | 5 | insoluble |
| 2.75 | | 23 | PEG(10K) | 5.2 | insoluble |
| 2.4 | | 23 | PEG(1K) | 5.5 | insoluble |

Figure 6:
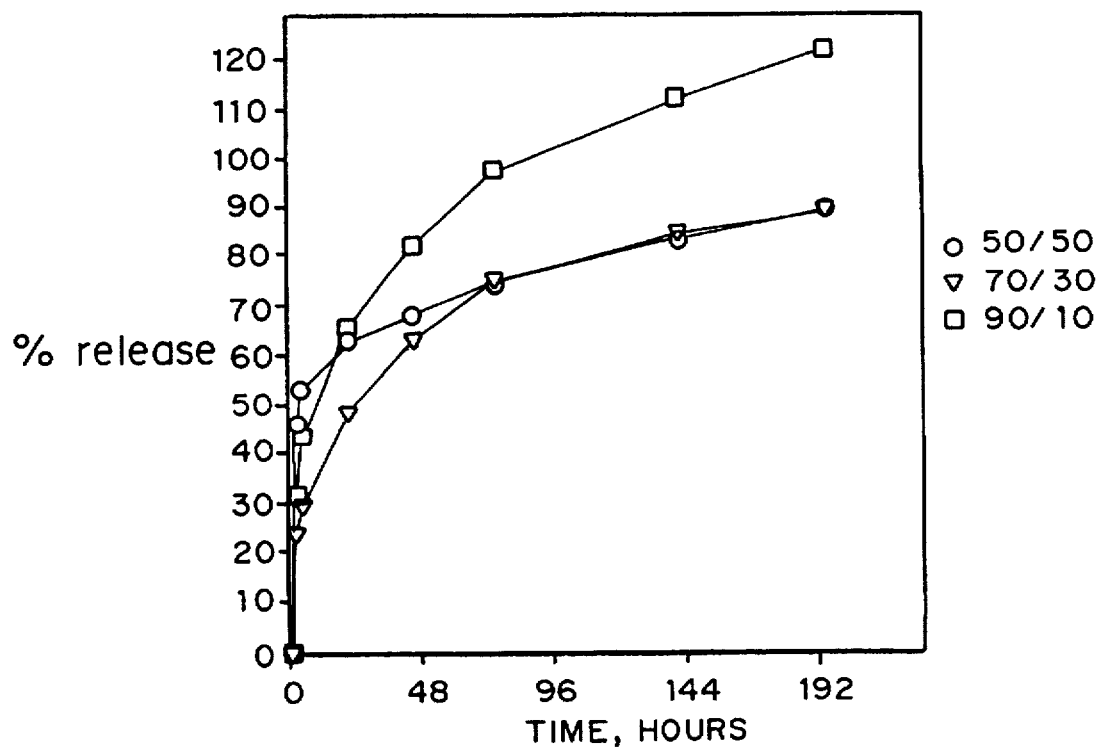
FIG. 6 is a graph of the release of chlorhexidine from SAIB/ethyl lactate (EtLac) as measured in percent release over time (hours) (50/50 SAIB/EtLac, open circle; 70/30 SAIB/EtLac, open downward-pointing triangle; 90/10 SAIB/EtLac, open square).
Figure 7:
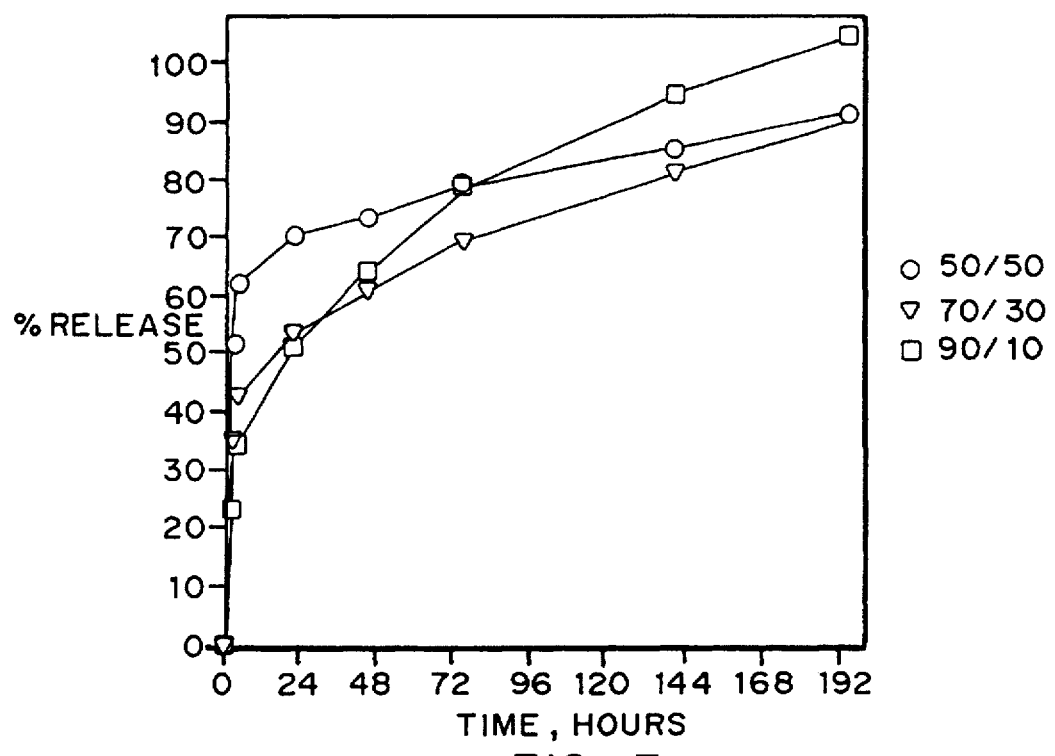
FIG. 7 is a graph of the release of chlorhexidine from SAIB/NMP as measured in percent release over time (hours) (50/50 SAIB/NMP, open circle; 70/30 SAIB/NMP, open downward-pointing triangle; 90/10 SAIB/NMP, open square).
Figure 8:
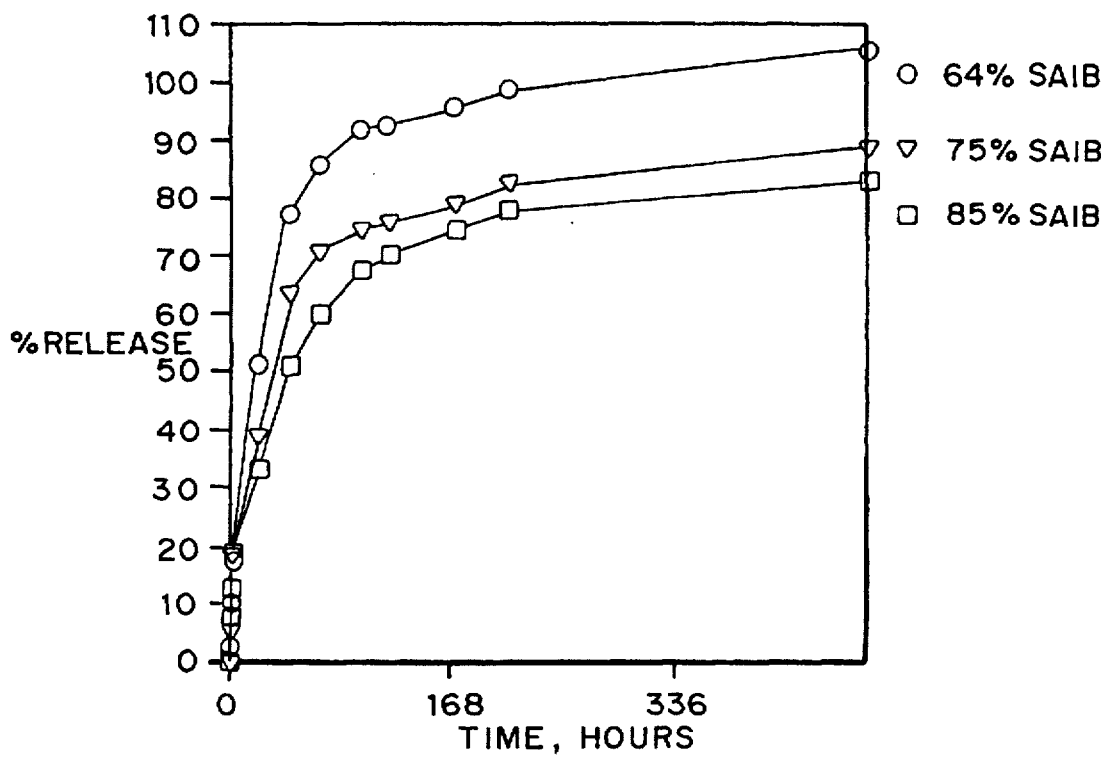
FIG. 8 is a graph of the release of chlorhexidine from SAIB/propylene carbonate as measured in percent release over time (hours) (64% SAIB, open circle; 75% SAIB, open downward-pointing triangle; 85% SAIB, open square).
Figure 9:
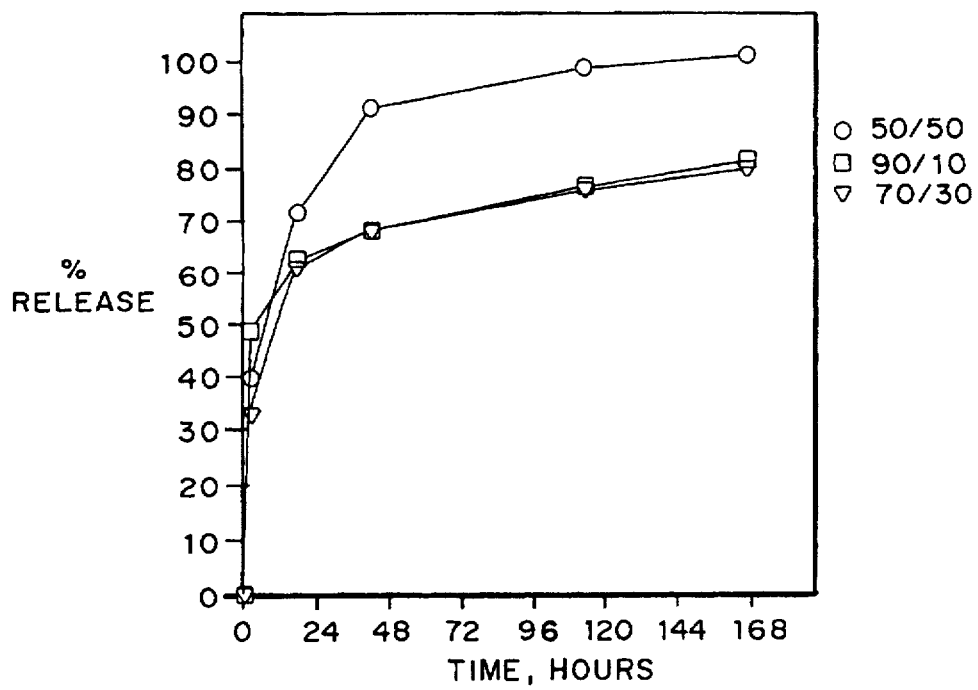
FIG. 9 is a graph of the release of 2.5% diclofenac from SAIB/triacetin as measured in percent release over time (hours) (50/50 SAIB/triacetin, open circle; 70/30 SAIB/triacetin, open downward-pointing triangle; 90/10 SAIB/triacetin, open square).
Figure 10:
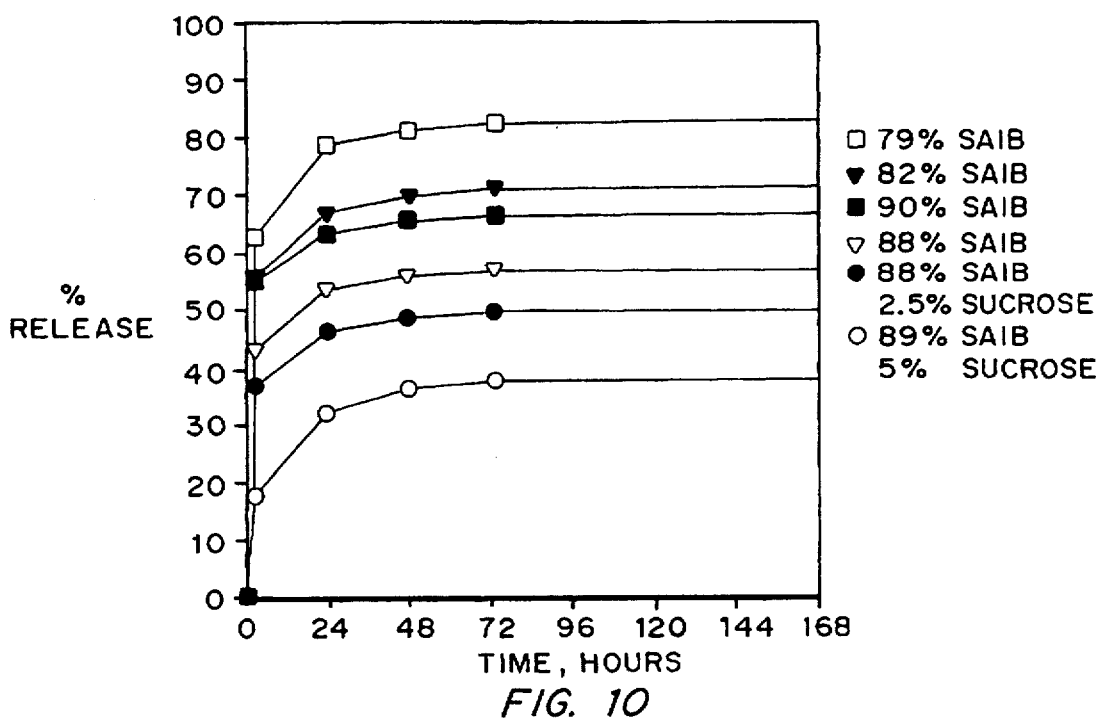
FIG. 10 is a graph of the release of 2.5% diclofenac from SAIB/ethanol (EtOH), with and without sucrose, as measured in percent release over time (hours) (79% SAIB, open square; 82% SAIB, closed downward-pointing triangle; 90% SAIB, closed square; 88% SAIB, open downward-pointing triangle; 88% SAIB, 2.5% sucrose, closed circle, 80% SAIB, 5% sucrose, open circle).
Figure 11:
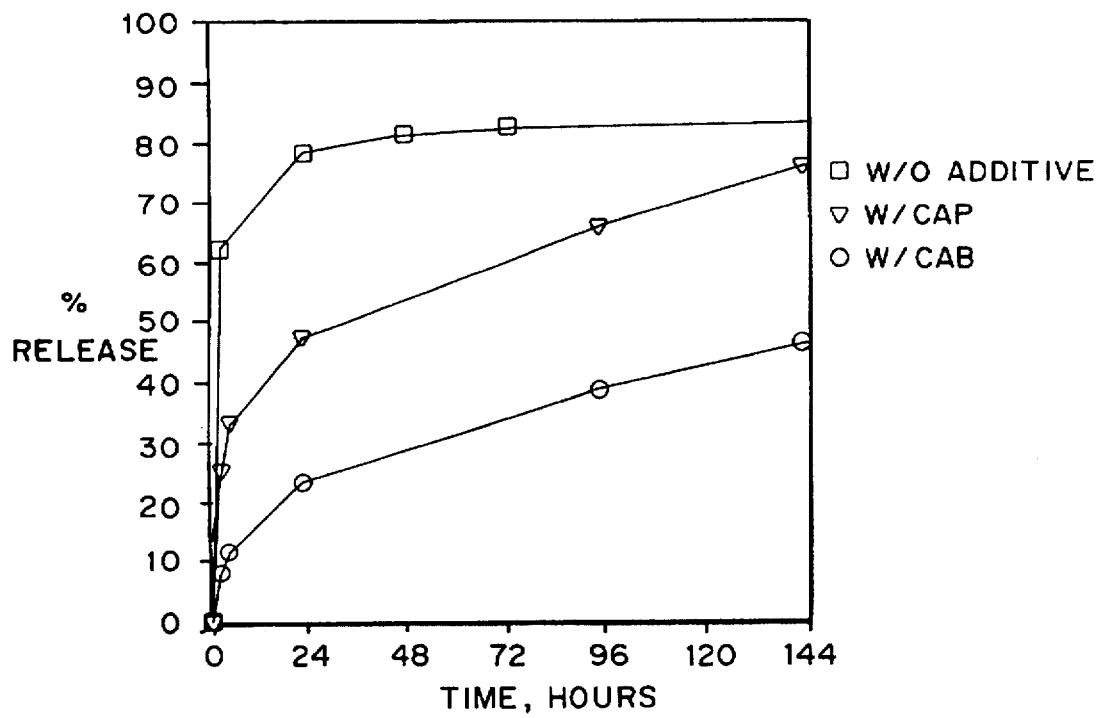
FIG. 11 is a graph of the release of 2.5% diclofenac from SAIB/EtOH, with and without additives, CAB and cellulose acetate propionate ("CAP"), as measured in percent release over time (hours) (without additive, open square; with CAP, open downward-pointing triangle; with CAB, open circle).
Figure 12:
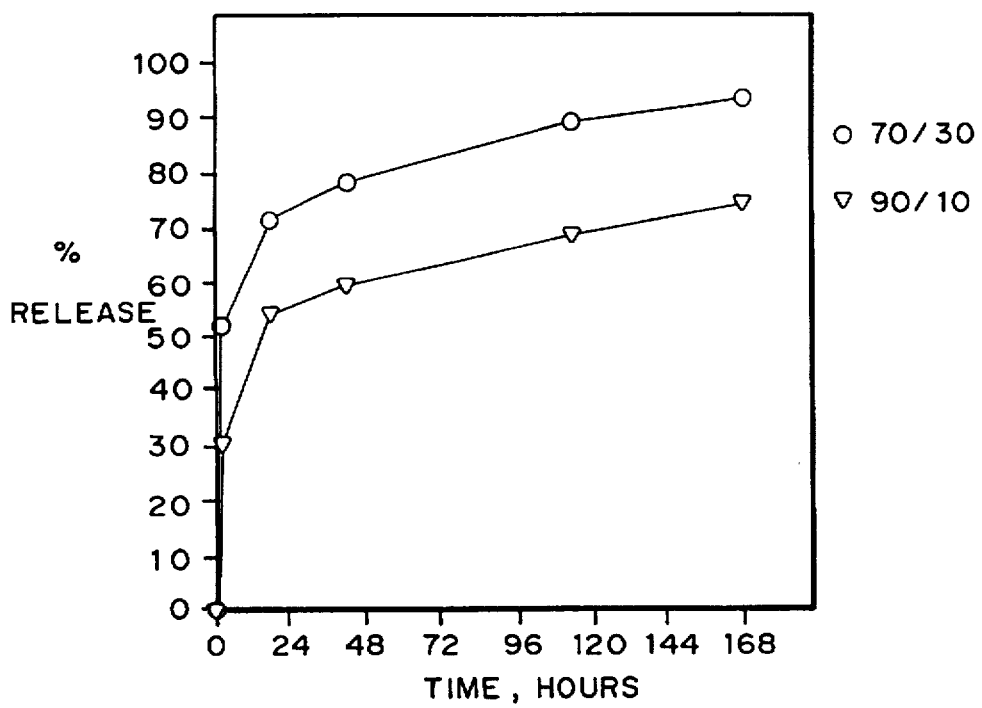
FIG. 12 is a graph of the release of 2.5% diclofenac from SAIB/dimethylsulfoxide (DMSO) as measured in percent release over time (hours) (70/30 SAIB/DMSO, open circle; 90/10 SAIB/DMSO, open downward-pointing triangle).

The release profile for chlorhexidene in various solvents is illustrated in FIGS. 6 to 8.

Optimization of the soluble amount of chlorhexidine in SAIB/EtOH/CAB was conducted. The results are shown in Table 6.

TABLE 6

| % drug | % EtOH | % CAB | solubility |
|---|---|---|---|
| 12 | 57.5 | 3 | insoluble at RT (soluble when heated) |
| 14.7 | 47.2 | 3.8 | soluble for a day or two |
| 15 | 51 | 3.4 | insoluble |
| 18 | 50.4 | 3.1 | insoluble |

EXAMPLE 6

The procedure of Example 3 was repeated using a series of formulations containing diclofenac sodium as the biologically active agent. Formulations containing various amounts of solvent, SAIB and additives were prepared. Diclofenac release slowed with increasing ratios of CAB:SAIB.

Formulations to which diclofenac was added as the biologically active substance are set forth below in Table 7.

TABLE 7

| % drug | Solvent | % solv | additive | % add | solubility |
|---|---|---|---|---|---|
| 2.68 | EtOH | 19.1 | — | — | insoluble |
| 2.48 | | 15.6 | — | — | insoluble |
| 2.40 | | 9.6 | — | — | insoluble |
| 2.68 | | 7 | — | — | insoluble |
| 2.43 | | 7.1 | sucrose | 2.6 | insoluble |
| 2.56 | | 3.6 | sucrose | 5.1 | insoluble |
| 2.39 | | 28.7 | CAB | 4.8 | soluble |
| 2.44 | | 28.6 | PEG(1K) | 4.8 | insoluble |
| 2.89 | | 28.7 | PVP(25) | 4.8 | insoluble |
| 2.38 | | 28.3 | PEG(10K) | 5.3 | insoluble |
| 2.35 | | 36.3 | CAP | 5.2 | soluble |
| 2.57 | Triacetin | 50 | — | — | insoluble |
| 2.89 | | 30 | — | — | insoluble |
| 2.43 | DMSO | 11.5 | — | — | insoluble |
| 2.58 | | 50 | — | — | soluble (but brown) |
| 2.45 | | 30.5 | — | — | insoluble |
| 2.36 | | 10.2 | — | — | insoluble |

The release profile for diclofenac in various solvents is illustrated in FIGS. 9 to 12.

EXAMPLE 7

The procedure of Example 3 was repeated using a series of formulations containing doxycyline as the biologically active agent. Formulations containing various amounts of solvent, SAIB and additives were prepared.

Formulations to which doxycycline was added as the biologically active substance are set forth below in Table 8.

TABLE 8

| % drug | Solvent | % solv | additive | % add | solubility |
|---|---|---|---|---|---|
| 5 | EtOH | 15 | — | — | insoluble |
| 2.56 | | 15 | — | — | insoluble |
| 4.97 | EtOAc | 30 | — | — | insoluble |
| 2.5 | EtLac | 30 | — | — | insoluble |
| 2.45 | PC | 30 | — | — | insoluble |
| 2.5 | GF | 30 | — | — | insoluble |
| 2.5 | DMSO | 30 | — | — | soluble temporarily |

A small amount of DMSO was used with the SAIB/EtOH/CAB combination to aid in the solubility of doxycycline. These formulations are shown below in Table 9.

TABLE 9

| % Doxy | % EtOH | % CAB | % DMSO | solubility |
|---|---|---|---|---|
| 3.01 | 49 | 6.7 | 7.6 | soluble |
| 4.03 | 47 | 8.9 | 7.9 | soluble |
| 3.07 | 42 | 5.6 | 7.4 | insoluble |
| 4.17 | 72 | 21 | 7.5 | soluble[note: no SAIB] |

EXAMPLE 8

The procedure of Example 3 was repeated using a series of formulations containing flurbiprofen as the biologically active agent. Formulations containing various amounts of solvent, SAIB and additives were prepared.

Formulations to which flurbiprofen was added as the biologically active substance are set forth below in Table 10.

TABLE 10

| % drug | Solvent | % solv | additive | % add | solubility |
|---|---|---|---|---|---|
| 2.48 | EtOH | 15 | — | — | soluble |
| 4.98 | EtOH | 15 | — | — | soluble |
| 9.98 | EtOH | 15 | — | — | soluble |
| 4.99 | EtOH | 45 | CAB | 5.0 | soluble |
| 9.92 | EtOH | 45 | CAB | 5.5 | soluble |

Figure 13:
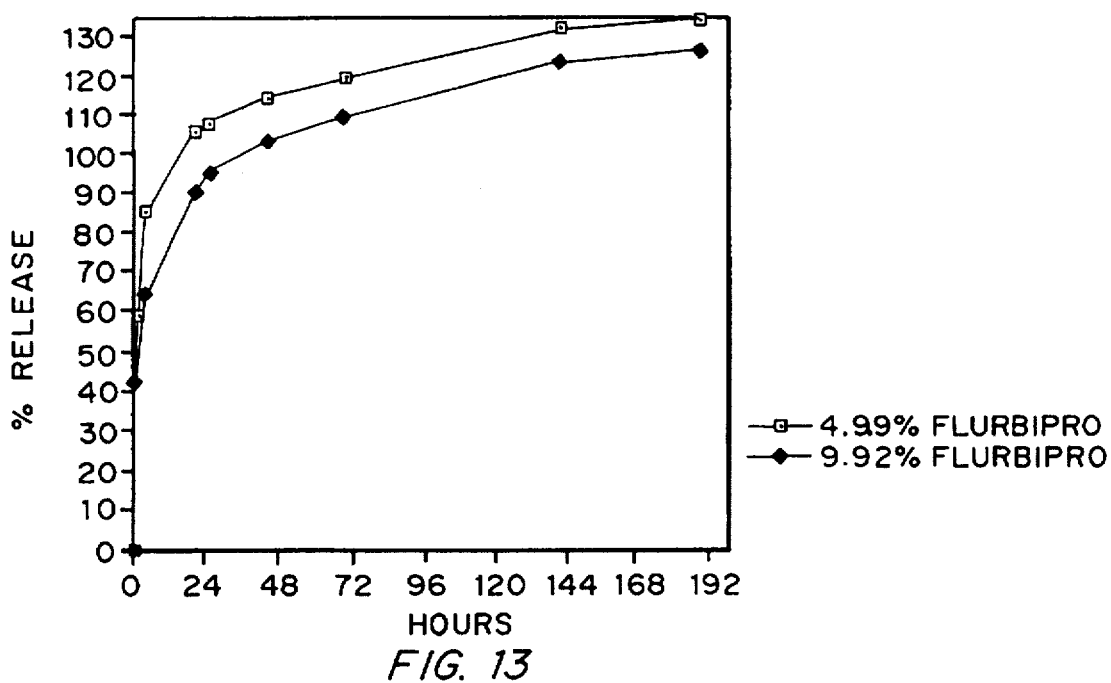
FIG. 13 is a graph of the release of flurbiprofen from SAIB/45%EtOH/5%CAB as measured in percent release over time (hours) (4.99% flurbiprofen, open square; 9.92% flurbiprofen, closed diamond).

The release profile for flurbiprofen is shown in FIG. 13.

EXAMPLE 9

The procedure of Example 3 was repeated using a series of formulations containing naproxen (free acid) as the biologically active agent. Formulations containing various amounts of solvent, SAIB and additives were prepared.

Formulations to which naproxen (free acid) was added as the biologically active substance are set forth below in Table 11.

TABLE 11

| % drug | Solvent | % solv | additive | % add | solubility |
|---|---|---|---|---|---|
| 5.2 | GF | 21 | — | — | soluble |
| 3.6 | GF | 37 | — | — | soluble |
| 4.1 | GF | 44 | — | — | soluble |

EXAMPLE 10

The procedure of Example 3 was repeated using a series of formulations containing naproxen (sodium salt) as the biologically active agent. Formulations containing various amounts of solvent, SAIB and additives were prepared.

Naproxen (sodium salt) is not soluble in EtOH and EtOAc. Formulations to which naproxen (sodium salt) was added as the biologically active substance are set forth below in Table 12.

TABLE 12

| % drug | Solvent | % solv | additive | % add | solubility |
|---|---|---|---|---|---|
| 5.2 | GF | 21 | — | — | insoluble |
| 3.4 | GF | 37 | — | — | soluble |
| 3.9 | GF | 44 | — | — | soluble |

Figure 14:
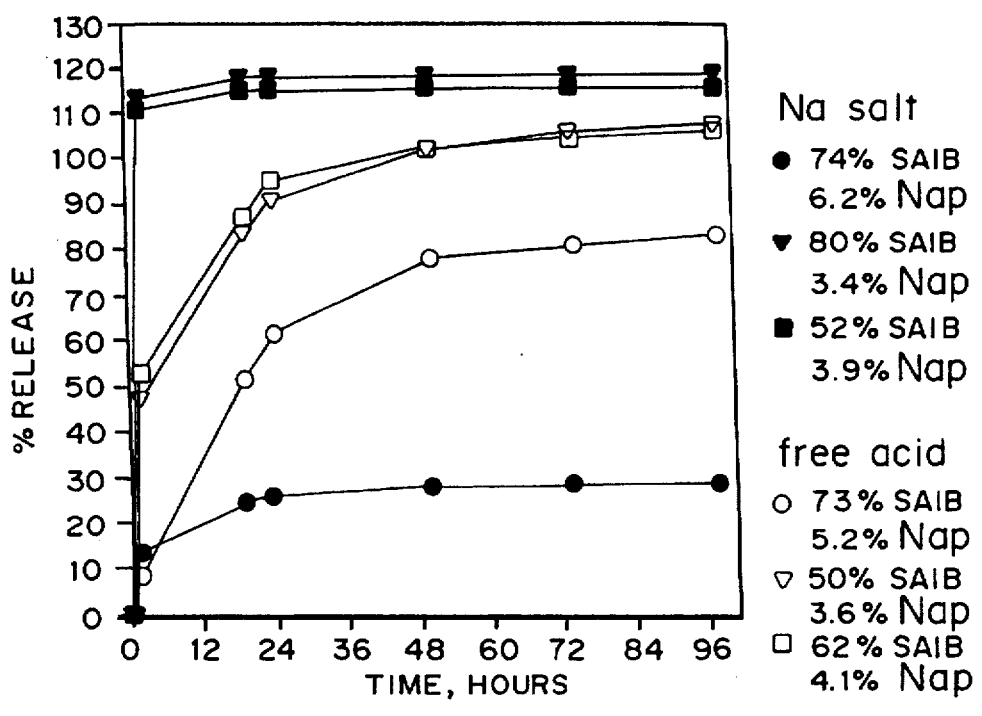
FIG. 14 is a graph of the release of naproxen (free acid or sodium salt) from SAIB/glycofurol as measured in percent release over time (hours) (73% SAIB, 5.2% naproxen (free acid), open circle; 60% SAIB, 3.6% naproxen (free acid), open downward-pointing triangle; 52% SAIB, 4.1% naproxen (free acid), open square; 74% SAIB, 5.2% naproxen (sodium salt), closed circle; 60% SAIB, 3.4% naproxen (sodium salt), closed downward-pointing triangle; 52% SAIB, 3.9% naproxen (sodium salt), closed square).
Figure 15:
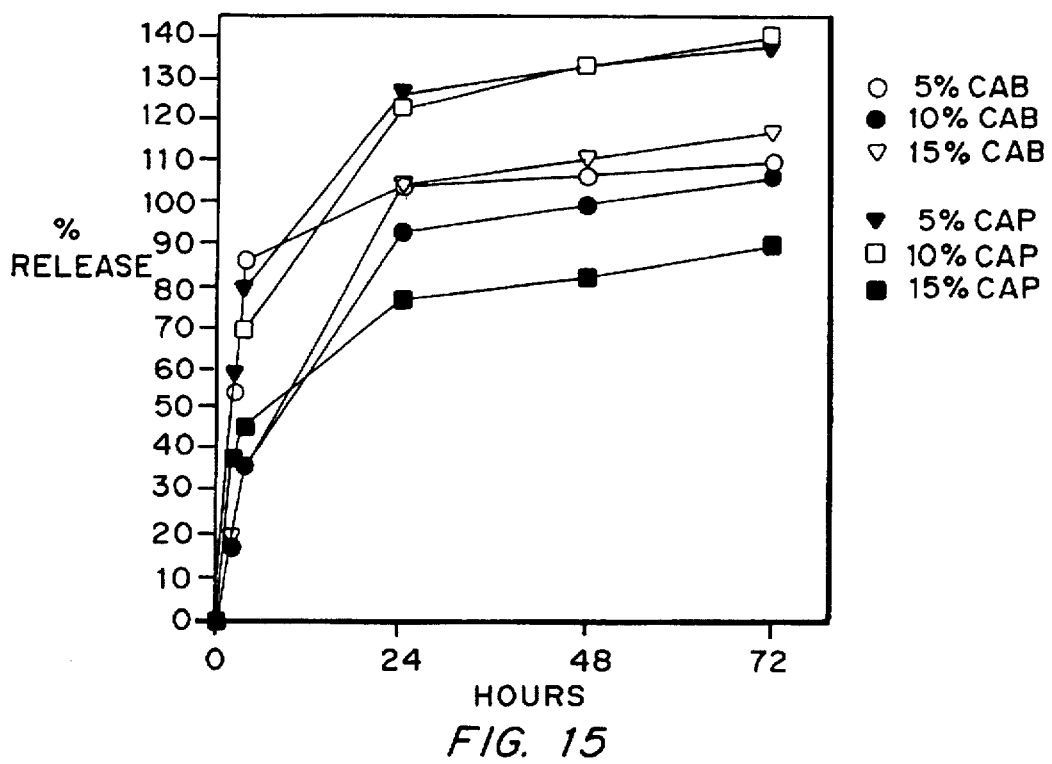
FIG. 15 is a graph of the release of 2.5% theophylline from SAIB(40%)/EtOH/CAB or CAP, as measured in percent release over time (hours) (5% CAB, open circle; 10% CAB, closed circle; 15% CAB, open downward-pointing triangle; 5% CAP, closed downward-pointing triangle; 10% CAP, open square; 15% CAP, closed square).

The release profile for naproxen (free acid and sodium salt) in various solvents is shown in FIG. 14.

EXAMPLE 11

The procedure of Example 3 was repeated using a series of formulations containing naproxen (sodium salt) and naproxen (free acid) as the biologically active agent. Formulations containing various amounts of solvent, SAIB and additives were prepared.

Formulations to which naproxen (sodium salt) and naproxen (free acid) were added as the biologically active substance are set forth below in Table 13.

TABLE 13

| % free acid | % Na salt | Solvent | % solv | solubility |
|---|---|---|---|---|
| 2.38 | 2.55 | PC | 20 | insoluble |
| 1.28 | 3.56 | GF | 20 | insoluble |
| 2.27 | 2.78 | EtLac | 30 | soluble |
| 2.49 | 2.55 | GF | 20 | soluble |

EXAMPLE 12

The procedure of Example 3 was repeated using a series of formulations containing theophylline as the biologically active agent. Formulations containing various amounts of solvent, SAIB and additives were prepared.

Formulations to which theophylline was added as the biologically active substance are set forth below in Table 14.

TABLE 14

| % drug | Solvent | % solv | additive | % add | solubility |
|---|---|---|---|---|---|
| 0.5 | EtOH | 15 | — | — | insoluble |
| 1 | EtOH | 15 | — | — | insoluble |
| 2.5 | EtOH | 15 | — | — | insoluble |
| 5 | EtOH | 15 | — | — | insoluble |
| 10 | EtOH | 15 | — | — | insoluble |
| 2.5 | EtOH | 53 | CAB | 5 | insoluble |
| 2.5 | EtOH | 47 | CAB | 10 | insoluble |
| 2.5 | EtOH | 43 | CAB | 15 | insoluble |
| 2.5 | EtOH | 53 | CAP | 5 | insoluble |
| 2.6 | EtOH | 48 | CAP | 10 | insoluble |
| 2.5 | EtOH | 43 | CAP | 15 | insoluble |
| 5.2 | EtOAc | 48 | — | — | insoluble |
| 4.8 | EtOAc | 29 | — | — | insoluble |
| 5.0 | EtOAc | 9.5 | — | — | insoluble |
| 5.0 | $\Phi CH_2OH$ | 48 | — | — | insoluble |
| 5.2 | $\Phi CH_2OH$ | 29 | — | — | insoluble |
| 5.0 | $\Phi CH_2OH$ | 11 | — | — | insoluble |
| 5.4 | EtOH | 10 | — | — | insoluble |
| 6.5 | EtOH | 20 | — | — | insoluble |
| 5.5 | EtOH | 30 | — | — | insoluble |
| 5.5 | EtOH | 25 | CAB | 5.5 | insoluble |
| 7.2 | EtOH | 34 | CAB | 5.4 | insoluble |
| 5.4 | EtOH | 45 | CAB | 5.9 | insoluble |

TABLE 14-continued

| % drug | Solvent | % solv | additive | % add | solubility |
|---|---|---|---|---|---|
| 5.1 | PC | 11 | — | — | insoluble |
| 5.5 | PC | 20 | — | — | insoluble |
| 5.5 | PC | 31 | — | — | insoluble |

Figure 16:
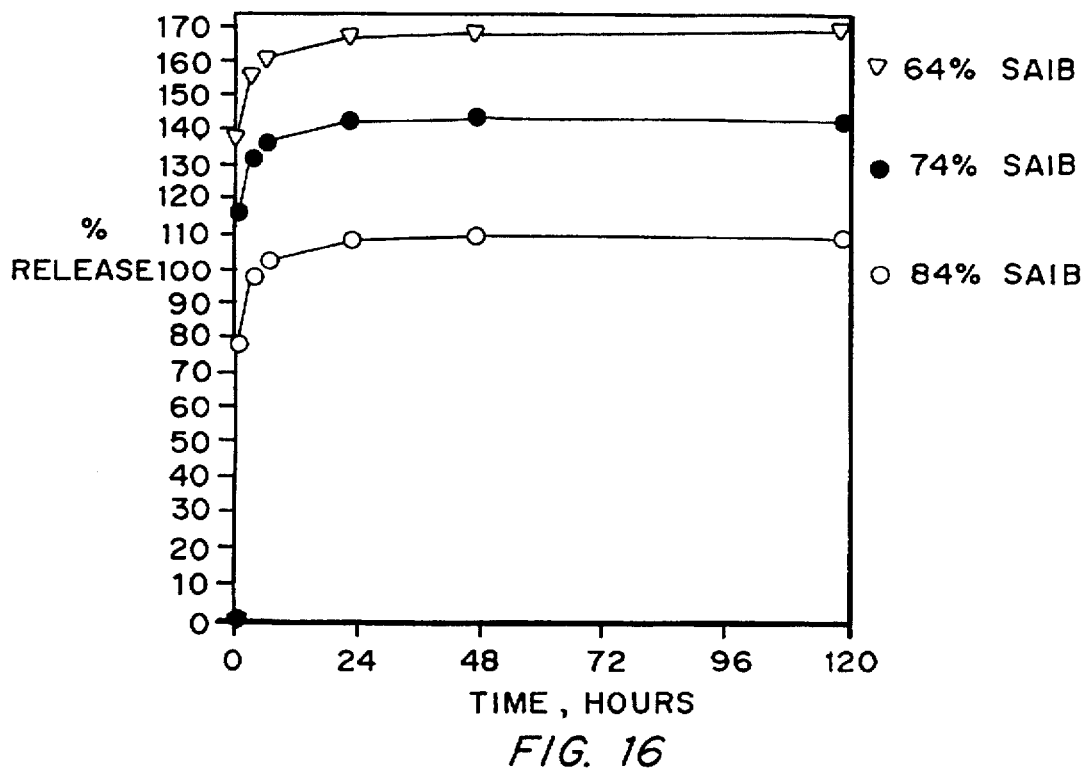
FIG. 16 is a graph of the release of theophylline from SAIB/propylene carbonate, as measured in percent release over time (hours) (64% SAIB, open downward-pointing triangle; 74% SAIB, closed circle; 84% SAIB, open circle).

The release profile for theophylline in propylene carbonate is shown in FIG. 16.

A release profile was attempted on the following formulations with theophylline but the samples were very cloudy. The amounts of materials in these formulations are shown below in Table 15.

TABLE 15

| % drug | Solvent | % solv | additive | % add | solubility |
|---|---|---|---|---|---|
| 4.9 | EtOH | 16 | PVP(K25) | 5.1 | insoluble |
| 5.0 | EtOH | 40 | PVP(K25) | 5.0 | insoluble |
| 5.1 | EtOH | 15 | PEG(1K) | 5.0 | insoluble |
| 5.0 | EtOH | 40 | PEG(1K) | 5.0 | insoluble |
| 4.9 | EtOH | 16 | PEG(10K) | 5.4 | insoluble |
| 4.9 | EtOH | 41 | PEG(10K) | 4.9 | insoluble |

EXAMPLE 13

A formulation was prepared with 80% SAIB and 15% ethanol, the resulting solution was loaded into an aerosol container. The solution was sprayed onto agar plates where it formed an adhesive continuous film.

EXAMPLE 14

A series of formulations were prepared with 80% SAIB, 0.02% methylene blue and varying ratios of ethanol to CAB, from 1:0 to 1:1. The formulations were sprayed onto gelatin. The dilution of the methylene blue into the gelatin slowed with increasing CAB contents.

EXAMPLE 15

SAIB was heated to 60° C. Separate formulations were made with 1,2,5 and 10% tetracycline. The formulations were loaded into a syringe equipped with a 21 gauge needle. The formulations were manually expelled from the syringe into 37° C. butter. The formulations could be easily expelled at temperatures of approximately 45° C.

EXAMPLE 16

Preparation and Properties of Mouthwash

Polyoxyethylene (7.680 g, 20 E.C.) almond oil (Crovol A-70), 4.042 g of decaglycerol tetraoleate (Caprol 10G40), and 11.721 g of medium-chain triglyceride (Neobee M-5) were combined in a suitable mixing vessel (jacketed, single-action, swept-surface kettle). The mixture was heated to about 65° C. Methyl paraben (0.500 g), 0.250 g of propyl paraben, 0.125 g of cetyl pyridinium chloride, 0.125 g of benzoic acid, and 0.625 g of sucrose acetate isobutyrate were mixed into the heated organic phase. The organic phase mixture was maintained at about 65° C. throughout the additional of components. Zinc gluconate (0.250 g), 0.125 g of sodium benzoate, 0.0625 g of citric acid, and 12.5 g of sorbitol were dissolved in 221.10 g of deionized water. The water phase mixture was heated to about 65° C. After both the organic phase and the water phase mixtures reach temperature, the water phase was slowly added to the oil phase with agitation. When the water phase had been completely added to the oil phase, 2 drops of green food coloring and 1.000 g of peppermint oil were added and thoroughly mixed into the formulation. The mixture was then quickly cooled to room temperature and packaged. Water loss during processing at this scale is about 10.1 g.

The finished product had the following composition.

TABLE 16

| Ingredient | wt % |
|---|---|
| PEG-20 Almond Oil | 3.07 |
| Medium-Chain Triglyceride | 4.69 |
| Decaglycerol Tetraoleate | 1.62 |
| Water | 84.4 |
| Peppermint Oil | 0.400 |
| Methyl Paraben | 0.200 |
| Propyl Paraben | 0.100 |
| Cetyl Pyridinium Chloride | 0.050 |
| Zinc Gluconate | 0.100 |
| Sorbitol | 5.00 |
| Sodium Benzoate | 0.050 |
| Citric Acid | 0.025 |
| Benzoic Acid | 0.050 |

EXAMPLE 17

A vascular graft was immersed in a solution of 61.8% SAIB, 10.0% CAB, and 28.2% EtOH, to which 1% heparin was added. The graft was drained of the solution, and rinsed with physiological saline. The vascular graft was implanted in a dog. After explantation the interior surface of the graft was free of clotted blood as compared to a control vascular graft.

EXAMPLE 18

Formulations of 5% CAB, 45% ethanol, and 50% SAIB were prepared. To these were added transforming growth factor-beta, in amounts from 0.05–0.0005%, or phenol in a range of 1–5.1%. The compositions were injected into the inguinal canal of a dog where they elicited a cellular response leading to occlusion of the canal.

EXAMPLE 19

Formulations of 10% CAB, 45% ethanol, and 45% SAIB were aerosoled onto the uterine horn of a rabbit, which had been surgically abraded. The areas did not all show elimination of the surgical adhesion on reexamination, however the article was well tolerated biologically.

EXAMPLE 20

Figure 17:
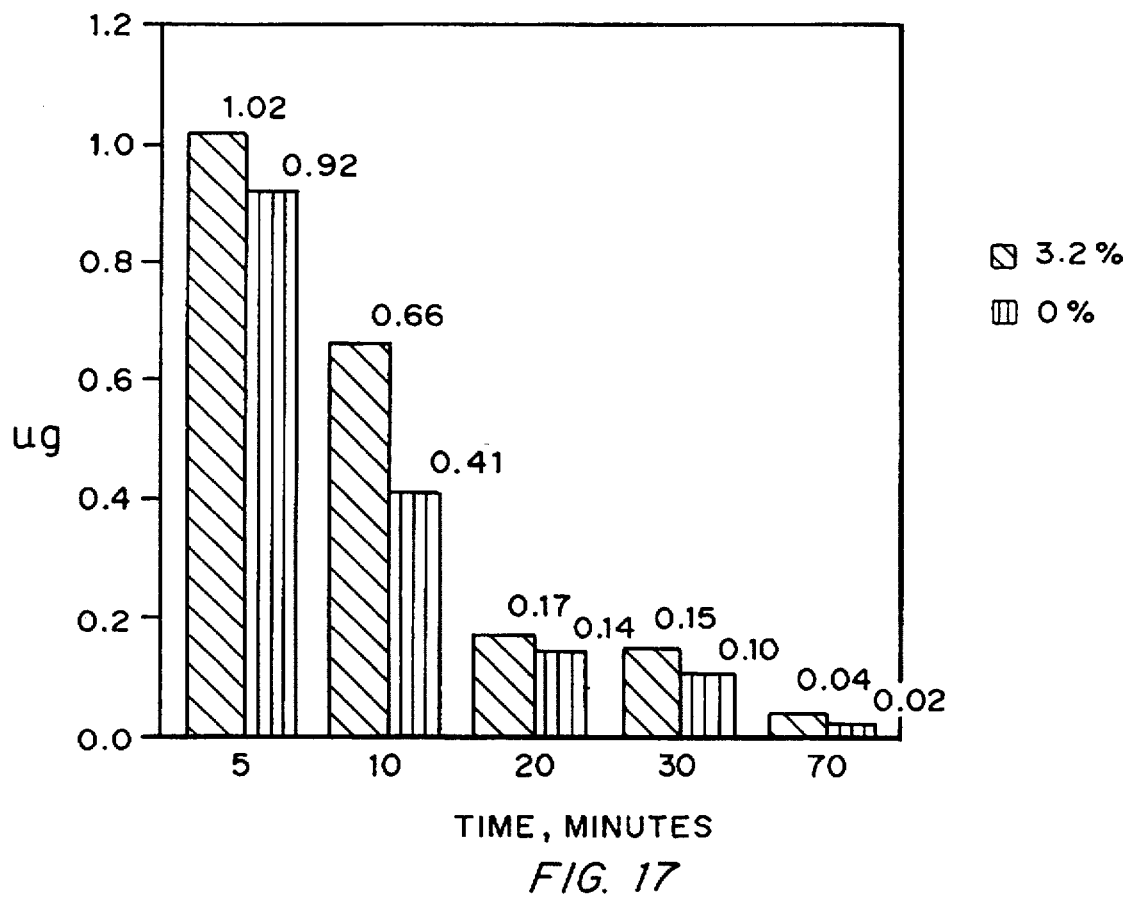
FIG. 17 is a graph of the release of two formulations. One formulation (black shading) contains 3.2% SAIB, 15.1% EtOH, 0.00395% methylene blue, and the remainder diH₂O. The other formulation (slanted shading) was 0% SAIB, 28.9% EtOH, 0.00395% methylene blue, and diH₂O.

FIG. 17 is a graph of the release of two formulations. One formulation (black shading) contains 3.2% SAIB, 15.1% EtOH, 0.00395% methylene blue, and the remainder diH$_2$O. The other formulation (slanted shading) was 0% SAIB, 28.9% EtOH, 0.00395% methylene blue, and diH$_2$O.

One inch strips of natural collagen were cut, rinsed in PBS (pH 6.8), submerged in the formulation for nine minutes, placed in clean test tubes and covered with PBS. At different time points the PBS was decanted and UV-analyzed; fresh PBS was added to the test tube containing the collagen. See FIG. 17.

Modifications and variations of the present invention, the compositions and methods of use thereof, will be obvious to those skilled in the art from the foregoing detailed description. Such modifications and variations are intended to come within the scope of the appended claims.

We claim:

1. A liquid composition for the delivery of biologically active substances comprising:
   (a) a non-polymeric, non-water soluble high viscosity liquid carrier material having a viscosity of at least 5,000 cP at 37° C. that does not crystallize neat under ambient or physiological conditions; and
   (b) a biologically active substance.

2. The composition of claim 1, wherein the non-polymeric non-water soluble liquid carrier material is sucrose acetate isobutyrate.

3. The composition of claim 2, wherein the non-polymeric non-water soluble liquid carrier material is present in an amount from about 99.5 percent to about 10 percent by weight, relative to the total weight of the composition.

4. The composition of claim 3, wherein the non-polymeric non-water soluble liquid carrier material is present in an amount from about 95 percent to about 25 percent by weight, relative to the total weight of the composition.

5. The composition of claim 2, wherein the composition further comprises a solvent in which the non-polymeric non-water insoluble liquid carrier material is soluble.

6. The composition of claim 5, wherein the solvent is selected from the group consisting of ethanol, dimethylsulfoxide, ethyl lactate, ethyl acetate, benzyl alcohol, triacetin, 2-pyrrolidone, N-methylpyrrolidone, propylene carbonate, and glycofurol.

7. The composition of claim 5, wherein the solvent is present in an amount from about 10 to about 50 percent by weight, relative to the weight of the composition.

8. The composition of claim 2, wherein the composition further comprises an additive.

9. The composition of claim 8, wherein the additive is selected from biodegradable polymers, non-biodegradable polymers, natural oils, synthetic oils, carbohydrates, inorganic salts, and inert organic compounds.

10. The composition of claim 8, wherein the additive is present in an amount in the range from about 1 to about 20 percent by weight, relative to the total weight of the composition.

11. The composition of claim 2, wherein the biologically active substance is selected from the group consisting of peptides, proteins, nucleoproteins, mucoproteins, lipoproteins, and synthetic polypeptides.

12. The composition of claim 3, wherein the non-polymeric non-water soluble high viscosity liquid carrier material is present in an amount from about 85 percent to about 45 percent by weight, relative to the total weight of the composition.

13. The composition of claim 2 suitable for topical administration.

14. The composition of claim 2 suitable for systemic administration.

15. The composition of claim 2 suitable for parenteral administration.

16. The composition of claim 5, wherein the solvent is selected from the group consisting of 2-pyrrolidone, N-methylpyrrolidone and ethanol.

17. The composition of claim 2, further comprising a lower viscosity liquid carrier material.

18. The composition of claim 17, wherein the lower viscosity liquid carrier material has a viscosity of less than 1000 cp.

19. The composition of claim 2, wherein the biologically active substance is useful for agricultural purposes.

20. The composition of claim 2, wherein the biologically active substance is useful for human therapy purposes.

21. The composition of claim 2, wherein the biologically active substance is useful for veterinary purposes.

22. The composition of claim 19, wherein the active agent is useful for the control of weeds.

23. The composition of claim 19, wherein the active agent is useful for the control of insects.

24. The composition of claim 19, wherein the composition is useful for the control of pests.

25. The composition of claim 20, wherein the biologically active agent is a steroid.

26. The composition of claim 2, wherein the biologically active agent is a vaccine.

27. The composition of claim 2, wherein the composition is useful to control lice.

28. The composition of claim 2, wherein the composition is useful to control dandruff.

29. The composition of claim 2, wherein the biologically active agent is theophylline.

30. The composition of claim 8, wherein the additive is cellulose acetate butyrate.

31. The composition of claim 2, wherein the biologically active agent is flurbiprofen.

32. The composition of claim 2, wherein the biologically active agent is naproxen.

33. The composition of claim 2, wherein the biologically active agent is chlorhexidine.

34. The composition of claim 2, wherein the biologically active agent is diclofenac.

35. The composition of claim 2, wherein the biologically active substance is a drug.

36. The composition of claim 2, wherein the biologically active substance is an anesthetic.

37. The composition of claim 2, wherein the biologically active compound is a peptide.

38. The composition of claim 2, wherein the biologically active compound is an estrogen.

39. The composition of claim 2, wherein the biologically active agent is a progesterone.

40. The composition of claim 2, wherein the biologically active agent is a hormone.

41. The composition of claim 2, wherein the biologically active agent is an antibiotic.

42. The composition of claim 2, wherein the biologically active agent is an antipsychotic.

43. The composition of claim 2, wherein the biologically active agent is tetracycline.

44. The composition of claim 2, wherein the biologically active agent is azithromycin.

45. The composition of claim 2, wherein the biologically active agent is a nucleoside or nucleotide.

46. The composition of claim 2, wherein the biologically active agent is dexamethasone.

47. The composition of claim 2, wherein the biologically active agent is 17-$\beta$-estradiol.

48. The composition of claim 2, wherein the biologically active agent is a progesterone and estradiol in combination.

49. The composition of claim 2, wherein the biologically active agent is a growth factor.

50. The composition of claim 8, wherein the additive comprises a poly(lactide).

51. The composition of claim 8, wherein the additive comprises a poly(lactide-co-glycolide).

52. The composition of claim 8, wherein the additive is a poly(glycolide).

53. The composition claim 8, wherein the additive is poly(caprolactone).

54. The composition of claim 8, wherein the additive is oxidized cellulose.

55. The composition of claim 8, wherein the additive is poly(D,L-lactic acid).

56. The composition of claim 8, wherein the additive is a nonbiodegradable polymer.

57. The composition of claim 8, wherein the additive is a biodegradable polymer.

58. The composition of claim 8, wherein the additive is polyvinyl pyrrolidone.

59. The composition of claim 8, wherein the additive is polyethylene glycol.

60. The composition of claim 8, wherein the additive is cellulose acetate butyrate.

61. The composition of claim 8, wherein the additive is cellulose acetate propionate.

62. The composition of claim 8, wherein the additive is peanut oil.

63. The composition of claim 8, wherein the additive is sesame oil.

64. The composition of claim 8, wherein the additive is sucrose.

65. The composition of claim 8, wherein the biologically active material is doxycycline.

66. The composition of claim 2, suitable for rectal administration.

67. The composition of claim 2, suitable for vaginal administration.

68. The composition of claim 2, suitable for nasal administration.

69. The composition of claim 8, wherein the additive is a carbohydrate.

70. The composition of claim 2, suitable for oral administration.

71. The composition of claim 2, wherein the biologically material is transforming growth factor-beta.

72. The composition of claim 2, wherein the biologically active material is a steroid.

73. The composition of claim 2, wherein the biologically active substance is a chemotherapeutic agent.

74. A method for the administration of the controlled release composition of claim 1, comprising the steps of
   (a) providing an amount of the controlled release composition; and
   (b) administering the composition to the host in a emulsion or in a solution.

75. A method for the administration of the controlled release composition of claim 1, comprising the step of administering the composition to the host via injection.

76. The composition of claim 1, wherein the biologically active material is an antiviral.

77. The composition of claim 1 useful to block surgical adhesions.

78. The composition of claim 1 useful in scaffolding, void filling, or tissue regeneration.

79. The composition of claim 1 for use to block the arterial supply of a tumor.

80. The composition of claim 2 useful as a tissue adhesive.

81. The composition of claim 2 useful in wound healing.

82. The composition of claim 2, wherein the biologically active molecule is heparin.

83. The composition of claim 1, wherein the carrier is disaccharide acetate butyrate.

84. The composition of claim 1, wherein the carrier is a disaccharide ester.

85. The composition of claim 1, wherein the biologically active substance is prepared by the steps comprising:
   (a) encapsulating the biologically active substance within a microsphere, to give an encapsulated microsphere; and
   (b) mixing the encapsulated microsphere with the carrier material;
   (c) to give the desired composition.

86. The composition of claim 1, wherein the biologically active substance is complexed with a complexing agent such as cyclodextrin.

87. The composition of claim 1, wherein the biologically active substance is in the form of a prodrug.

88. The composition of claim 1, wherein the composition is placed within a gelatin capsule for oral administration.

89. The composition of claim 1, wherein the composition is encapsulated within a microsphere or microcapsule.

90. The composition of claim 40, wherein the microsphere is a biodegradable polymer.

91. The composition of claim 1, wherein the controlled release formulation is associated with inert pharmaceutical excipients, said excipients optionally processed into spheres or other shapes and incorporated into a dosage form.

92. The composition of claim 2, wherein the biologically active material is selected from the group consisting of a nucleic acid, a nucleotide, nucleoside, or oligonucleotide.

93. The composition of claim 2, wherein the biologically active material is a gene.

94. The composition of claim 2, wherein the biologically active material is a lipid.

95. The composition of claim 2, wherein the biologically active material is a vitamin.

* * * * *